(12) United States Patent
Sandholm

(10) Patent No.: US 11,373,111 B2
(45) Date of Patent: Jun. 28, 2022

(54) EDGE TESTS IN BARTER EXCHANGES

(71) Applicant: Tuomas Sandholm, Pittsburgh, PA (US)

(72) Inventor: Tuomas Sandholm, Pittsburgh, PA (US)

(*) Notice: Subject to any disclaimer, the term of this patent is extended or adjusted under 35 U.S.C. 154(b) by 428 days.

(21) Appl. No.: 15/703,516

(22) Filed: Sep. 13, 2017

(65) Prior Publication Data

US 2018/0032688 A1 Feb. 1, 2018

Related U.S. Application Data

(63) Continuation-in-part of application No. 14/215,648, filed on Mar. 17, 2014, now abandoned.

(60) Provisional application No. 61/803,106, filed on Mar. 18, 2013.

(51) Int. Cl.
*G06N 7/00* (2006.01)

(52) U.S. Cl.
CPC .................... *G06N 7/005* (2013.01)

(58) Field of Classification Search
CPC .. G06Q 50/22; G06Q 10/087; G06Q 10/0875; G06N 7/005; G06N 20/00; G06N 3/08; G06F 19/328
USPC .......................................................... 705/2
See application file for complete search history.

(56) References Cited

U.S. PATENT DOCUMENTS

2005/0010437 A1* 1/2005 Abukwedar .......... G06Q 50/22
705/2

FOREIGN PATENT DOCUMENTS

WO    WO-0132016 A2 *  5/2001   ............. G16H 10/40

OTHER PUBLICATIONS

Abraham, David John; Matching markets: Design and analysis; Carnegie Mellon University. ProQuest Dissertations Publishing, 2009. 3383406. (Year: 2009).*

* cited by examiner

*Primary Examiner* — Hiep V Nguyen
(74) *Attorney, Agent, or Firm* — Ference & Associates LLC

(57) ABSTRACT

An embodiment provides a system including, but not necessarily limited to: a processor; a memory in communication with the processor; and computer readable program executable by the processor and configured to: receive, for one or more edges, testing data; store, for the one or more edges, testing data; create, by preferring successful edges over untested edges, an exchange plan, wherein, the exchange plan comprises one or more edges. Other aspects are described and claimed.

23 Claims, 9 Drawing Sheets

EDGE TESTS IN BARTER EXCHANGES

CLAIM FOR PRIORITY

This application is a continuation application which claims priority to U.S. patent application Ser. No. 14/215,648 which claims priority from U.S. Provisional Application No. 61/803,106, filed on Mar. 18, 2013, both of which are incorporated by reference as if fully set forth herein.

BACKGROUND

Barter markets (also referred to herein as "barter exchanges") operate as follows. The barter market operator facilitates the collection and storage of information from various participants about the items that the participants are willing to trade or give away and the items they desire to receive. Based upon this information, the barter market operator identifies items to be traded from one participant to another. In both the commercial and medical settings, the planning of such trades is desirable so that the maximum number or quality of successful trades might be accomplished in an exchange plan.

BRIEF SUMMARY

In summary, one aspect provides a system comprising: a processor; a memory in communication with the processor; and computer readable program executable by the processor and configured to: receive, for one or more edges, testing data; store, for said one or more edges, testing data; create, by preferring successful edges over untested edges, an exchange plan, wherein, said exchange plan comprises one or more edges.

Another aspect provides a program product comprising: a non-transitory computer readable storage medium having computer readable program code embodied therewith, the computer readable program code configured to operate a computing device to perform acts comprising: receiving, for one or more edges, testing data; storing, in memory, for said one or more edges, testing data; creating, using a processor, by preferring successful edges over untested edges, an exchange plan, wherein, said exchange plan comprises one or more edges.

A further aspect provides a method comprising: receiving, for one or more edges, testing data; storing, for said one or more edges, testing data; creating, by preferring successful edges over untested edges, an exchange plan, wherein, said exchange plan comprises one or more edges For a better understanding of embodiments, together with other and further features and advantages thereof, reference is made to the following description, taken in conjunction with the accompanying drawings, and the scope of the invention will be pointed out in the appended claims.

DETAILED DESCRIPTION

Figure 1A:
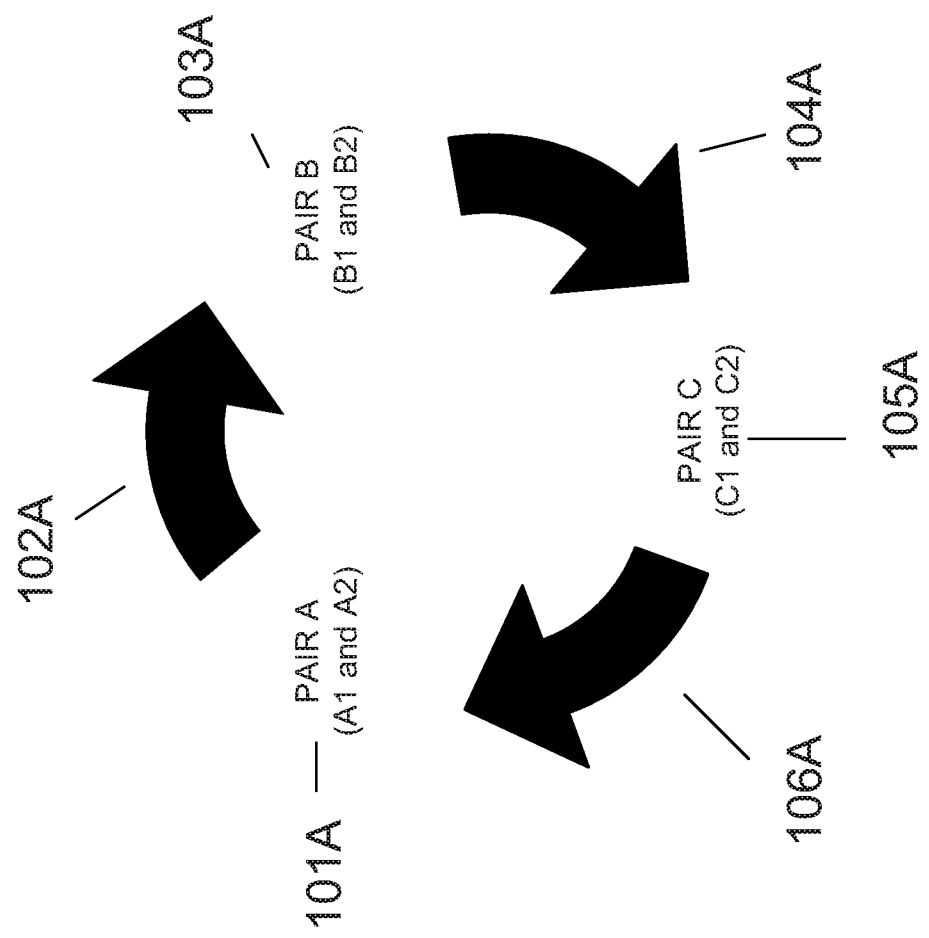
FIG. 1A describes an example barter cycle in some embodiments.
Figure 1B:
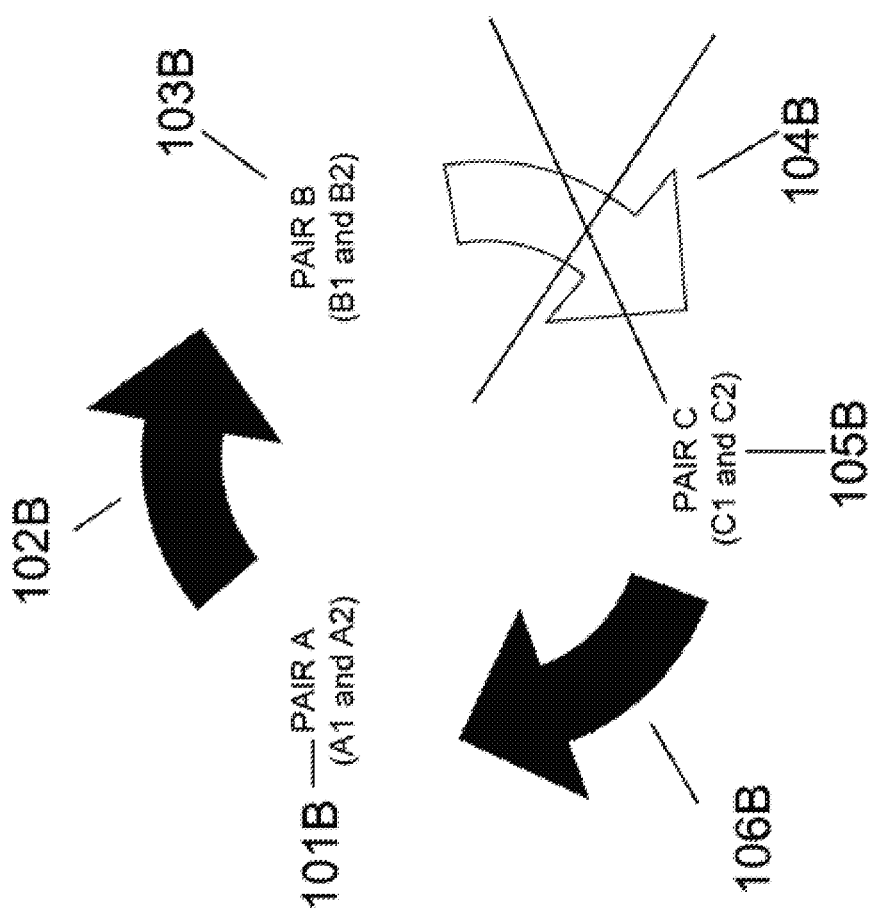
FIG. 1B describes an example barter cycle in some embodiments.
Figure 8:
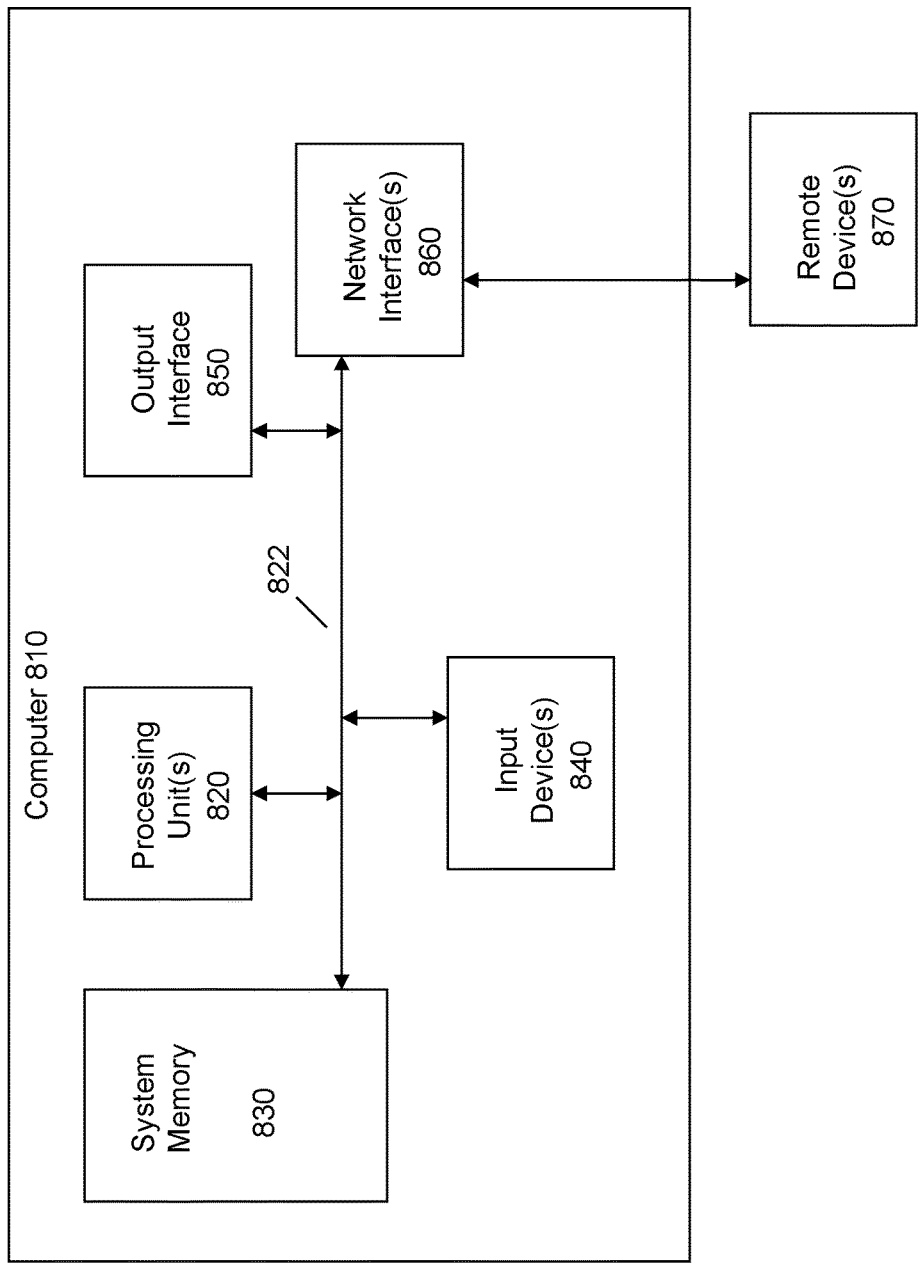
FIG. 8 illustrates an example computer.

It will be readily understood that the components of the embodiments, as generally described and illustrated in the figures herein, may be arranged and designed in a wide variety of different configurations. Thus, the following more detailed description of the embodiments of the apparatus, system, and method of the present invention, as represented in FIGS. 1A-1B through 8 is not intended to limit the scope of the embodiments of the invention, as claimed, but is merely representative of selected embodiments of the invention.

Reference throughout this specification to "one embodiment" or "an embodiment" (or the like) means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

Furthermore, the described features, structures, or characteristics may be combined in any suitable manner in one or more embodiments. In the following description, numerous specific details are provided, to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

For purposes of clarity throughout this disclosure, the following terminology will be used consistently. A vertex refers to a node in a barter exchange. Embodiments provide that in most barter exchanges, a vertex is one trader that gives and/or takes items. Trades between vertices are accomplished by constructing and executing edges (which may also be referred to as legs).

The illustrated embodiments of the invention will be best understood by reference to the drawings, wherein like parts are designated by like numerals or other labels throughout. The following description is intended only by way of example, and simply illustrates certain selected embodiments of devices, systems, and processes that are consistent with the invention as claimed herein.

The remainder of the disclosure begins with a general overview of the instant invention, and then proceeds to give a more detailed description of preferred embodiments of the invention with reference to the accompanying figures.

Embodiments provide that trades may be accomplished between vertices in cycles and/or chains. In a cycle, the trader typically gives and takes. While in the beginning of a chain, the trader just gives and at the end of a chain he or she just takes. An edge connotes a potential trade between two vertices in a cycle or chain. A barter exchange plan might include multiple cycles and/or chains to accomplish the multiple desired trades or donations.

In organ exchange, there can be at least two types of vertices. A vertex might be (1) a "pair" comprising a patient and one or more willing donors, or (2) an altruist. Typically in a pair, a donor is only willing to donate if that pair's patient receives an organ. In contrast, an altruist typically does not come with a patient, and the altruist is willing to donate without expecting or getting anything in return. Typically an altruist is needed to start a chain. Cycles, and other parts of chains except the altruist who starts a chain, typically consist of pairs.

In barter exchanges, an algorithm might be used to find a good combination of cycles and/or chains. This is referred to as an exchange plan. In one non-limiting example, kidney exchanges may rely upon such algorithms so as to maximize an objective. The objective can be, for example, the number of matched edges, and it can include quality aspects of those edges as well.

One non-limiting example of a vertex in an exchange plan for a kidney exchange would be a husband and a wife, wherein the husband is willing to donate a kidney into the kidney exchange program in return for his wife receiving a kidney from the kidney exchange program. In this example, the husband and wife are not compatible for purposes of such an organ exchange, that is, the husband cannot donate to the wife. The husband and wife would thus be placed as a vertex into the pool of potential vertices until a match could be found. Additionally, because the husband will only donate if his wife receives a kidney, the system will interconnect the husband and wife so that the husband will only be allowed to donate if his wife is matched.

In another non-limiting example, an altruist is willing to donate a kidney to any patient in need of that kidney. The altruist does not come with another person seeking to receive a kidney. Thus, if the altruist gets matched, the altruist begins a chain in which he expects and will receive nothing in return. For this example, we will assume that the altruist matches the wife in the above example. The altruist donates to the wife. The husband, who is not compatible with his wife, can then be asked to donate into the exchange when a compatible patient is found. In this way the chain might continue.

Creating exchange plans for items, for example, organs, partial organs, or commercial goods and services, and intangible rights involves many barriers. For example, in organ or partial organ donation, such barriers may include the dynamically changing medical condition of organ donors and patients. Such changes might be health or status of certainty for matching, e.g., of blood crossmatch failure, tissue crossmatch failure, or health of the donor or potential recipient, e.g., sick with cold, running fever, no longer alive. Indeed, it is particularly challenging in kidney exchange because about 90% of matches fail in the two or so months between the time when the exchange plan is made and the surgery is supposed to take place. A major reason for this is that some of the edges that seem compatible up front turn out to be incompatible after all in light of more detailed testing during that two-month period.

In creating exchange plans, it may be useful to perform testing of one or more (but typically not all, due, for example, to logistical or financial constraints) edges between vertices to determine which edges will fail. This is because these failed edges will cause the planned cycle or chain within which the failed edge is located to fail. This information may be useful in creating an overall successful exchange plan. Accordingly, an example embodiment provides a method of testing for compatibility of one or more of selected edges. Test data for one or more of the tested edges is then stored, e.g., saved in computer memory. Test data includes information about edges that are successful as well as edges that failed; there can also be degrees of success. The failed edges are excluded (potentially not permanently, because the edge status can change over time) from any future exchange plans. The vertices of failed cycles and chains are typically placed back into the pool for possible matching in the future. Part of the present invention is that identifying information about successfully tested edges is stored in memory, and is assigned a dynamic priority (typically higher than that of untested edges) for use in a future exchange planning.

Using the system and techniques as described herein provide a technical improvement to conventional barter exchanges. In conventional barter exchanges, for example, book clubs, clothing cyclers, and the like, a person typically advertises that they have something they would like to give up in order to gain another thing. Other people then must seek out the advertisements and determine whether they have something the person is willing to exchange for. A couple of problems exist with such a system. First, the exchangers must find each other, which means that a long cycle or chain is difficult to identify or make. For example, a long barter cycle may include more than two people, where the first person has something for exchange and wants a particular item, the second person wants the object that the first person has and has a particular item they are willing to give up but it is not the item the first person wants, and a third person wants the item the second person has and has an item to give up that matches the item the first person wants. Thus, in order for this cycle to work, the first person has to give his/her item to the second person, the second person gives his/her item to the third person, and the third person gives his/her item to the first person so that everyone has what they want. This is a very simplified example and is still complicated. When the number of things in the barter exchange, which can include both barter cycles and barter chains, increases the exchange plan gets significantly more complicated.

Additionally, in the case of organ donation, other factors have to be accounted for in order for an exchange to occur. For example, organ donations require tissue matching, health of a patient and/or organ, blood matching, preparation time for a patient/organ, criticality of an exchange, and the like. Due to these factors, the exchange is not just a simple match of one person wanting an item and having an item for exchange and the other person wanting that item and willing to provide the requested item. Thus, for these types of barter exchanges, creating a barter exchange plan including barter cycles and barter chains is very difficult, particularly when the number of people and/or organs involved in the exchange is numerous.

Additionally, in conventional person-to-person barter transactions, the exchange may not result in an optimal barter exchange. As an example, in a typical barter exchange the people do not take into account which exchanges between people would result in the most number of matches and/or successful exchanges. For example, in a barter exchange with four people there may exist more than one way to exchange objects between people that would result in at least one person gaining a desired item. However, there may only be one way to exchange the objects among the group in order to ensure that all the people gain the desired items. However, in conventional barter exchanges, no one may figure out what the optimal exchange plan would be to ensure the most exchanges occur. Additionally, as the number of objects within the exchange, the number of exchanges, and the number of factors increase, generation of an optimal barter exchange plan may be impossible using conventional "pen and paper" techniques.

Accordingly, an embodiment employs a computer to generate a barter exchange plan, which may include an optimal plan. The computer is able to process the amount of information, including a large number of possible exchanges, a large number of factors for each exchange, and a larger number of people within the exchange required to create the desired barter exchange plan, particularly an exchange plan that results in the most number of matches and exchanges. In a barter exchange, typically some algorithm is run (by computer or manually) to find good cycles and/or chains, which then constitute what we will call the exchange plan. Often, before the cycle or chain actually is executed, the legs (a.k.a. edges) in it are tested more thoroughly to see whether they are actually executable. For example, in kidney exchange a crossmatch is conducted where the planned donor's and planned recipient's bloods are mixed; if the mixture coagulates, that planned transplant is not executable because the planned donor and patient are medically incompatible. Typically if that test[1] fails, that cycle fails. Similarly, if a test of an edge in a chain fails, that chain fails. (Re-planning can be done to plan a different chain and/or cycle in its place.) The failure is typically recorded and the failed edge will not be allowed to be (at least until the status of that planned patient and donor changes) part of future exchange plans.

[1] We will use the singular for the test, but anyone knowledgeable in the art will appreciate the fact that there can be a sequence of tests for any given leg.

The invention here is that not only can we use information from failed tests but we can also use information from successful tests. One might think that there is no reason to incorporate such information because the planned legs for which the test succeeds proceed to execution. However, that reasoning is flawed for at least the following reasons. First, even if a leg passes the test, other legs in its chain or cycle may fail their tests in which case the entire cycle or chain may fail. Second, there may be other reasons why the leg fails to proceed to execution even if the test succeeds. Accordingly, we store the information about successful tests of legs and use it in future planning. One motivation is that legs whose tests succeeded are more promising for future matching than untested legs—because the former are less likely to fail to go to execution in the future if matched.

It will be appreciated by those skilled in the art that there are myriad methods of assigning priority to good edges and this disclosure contemplates all of those methods, though only a few are discussed herein. Thus, in one non-limiting example of organ exchanges, embodiments provide that in any pool there are untested edges (that is, edges where it has not been tested whether the planned donor from one pair is compatible with the planned recipient patient from another pair), there are tested edges that are successful, i.e., compatible, and there are tested edges that are failed, i.e., incompatible. Some embodiments provide that in constructing exchange plans, the failed edges should be distinguished and treated differently from the untested and tested and successful edges. Accordingly, embodiments provide that successful edges are preferred over untested edges in constructing future exchange plans.

A technical improvement provided by an embodiment is that information about edges that are successfully tested is stored for future planning along with information about failed edges and untested edges. By storing and re-testing the successfully tested edges along with failed edges and untested edges embodiments provide that the final exchange plan which is constructed ensures an optimal number of exchanges are effectuated for the greatest number of participants. For example in organ exchanges, by preferring successful edges over untested edges, an exchange plan may ultimately be constructed that saves the most number of lives waiting for compatible and available organ donors.

Another technical improvement described by an embodiment is that the following pseudocode may be used for finding an exchange plan that is the highest expected value combination of disjoint cycles and chains: (1) Generate all cycles in the input graph (no longer than a cycle-length cap if such a cap is desired.) This may be done using a depth-first search in the input graph. Embodiments describe that a depth-first search is an algorithm for searching a tree or graph data structure. In a depth-first search, one starts at the root, selecting a node and explores as far as possible along each branch before backtracking; (2) Generate a binary variable for each such cycle; (3) Generate all chains (no longer than a chain-length cap if such a cap is desired). This can be done using depth-first-search in the input graph; (4) Generate a binary variable for each such chain; (5) For all pairs of structures (cycles and chains), if the two structures in the pair share a vertex, then include a constraint that states that no more than one of the respective two binary variables can take on value 1. Value 1 represents that structure being included in the exchange plan, and value 0 represents that structure not being included in the exchange plan; (6) Set the objective of the problem to be maximizing expected value. In other words, if we denote the binary variables by $x_i$ and the expected values of the respective structures (as defined above) by $v_i$, the mathematical objective is max $\Sigma_i v_i * x_i$; (7) Run an integer program solver software package, such as IBM® ILOG CPLEX Optimization Studio or Gurobi Optimizer or a custom solver, to solve this model. Embodiments describe that finding the optimal trades through chains and cycles is an optimization problem that belongs to the infamous complexity class of NP-hard problems. This class of problems is too hard for humans to solve. The number of combinations of chains to consider (to sift through and evaluate) grows rapidly to millions and even numbers greater than the number of atoms in the universe. Embodiments must be accomplished using special purpose computers. Thus, embodiments describe that by using the technical improvement of the pseudocode, an optimized barter chain may be produced. As demonstrated, such optimization was not possible in conventional methods.

Turning now to the Figures, FIG. 1A-1B describes, a non-limiting example of an organ exchange, a barter cycle consisting of three vertices (each of the vertices having one donor and one patient). Such cycles may be implemented by computers and attendant program products. In this non-limiting example shown in FIG. 1A-1B, one of the originally matched edges fails due to later discovered incompatibility. In this example embodiment, each donor is designated with a "1" next to his or her vertex letter and each patient is designated with a 2 next to his or her vertex letter. The donor and the patient in each pair have agreed with the exchange that if the patient receives a donation, the donor will donate to another patient who is in search of a donation but does not match their own donor. Embodiments provide also that the donor and patient within a pair might be compatible but not the most suitable for each other.

In accordance with one example embodiment, in FIG. 1A-B, an exchange plan for an organ exchange has been created that comprises at least one barter cycle. PAIR A (A1 and A2) at 101A-B, PAIR B (B1 and B2) at 103A-B, and PAIR C (C1 and C2) at 105A-B are in a cycle in an example exchange plan. Continuing with FIG. 1A, A1 has been matched to B2 such that A1 may donate an organ, partial organ or other item wanted by B2. Thus, the exchange plan includes an edge 102A between A1 and B2. Likewise, B1 has been matched to C2 and an edge is planned between B1 and C2. Finally, a match has been found between C1 and A2 such that an edge in the cycle is planned at 106A.

Now turning to FIG. 1.B, after running a test for compatibility, e.g. blood crossmatch (where blood samples from the planned donor and the planned recipient are mixed together to see whether or not the mixture coagulates, which would indicate incompatibility), between B1 and C2, an incompatibility has been identified. The edge at 104B is now a "failed" or a bad edge, though early testing indicated compatibility. The entire example exchange plan fails because the edge at 104B failed. Thus, the failed edge at 104B, i.e., the exchange between B1 and C2, will not be used in constructing a future exchange plan. Embodiments provide that the remaining edges at 102A-B and 106A-B are still good and should be placed back into the pool of edges for constructing future exchange plans. According to some embodiments, the good edges at 102A-B and 106A-B are placed into the same pool but given a dynamic priority such that that these good edges will be preferred for use over other edges in constructing a future exchange plan.

Some embodiments provide that a dynamic priority may be accomplished by assigning weights to the good edges. Still other embodiments provide that the dynamic priority may be accomplished by assigning success probabilities. Further embodiments provide that edges can be assigned a weight and a probability; these can then be used to compute, for example, the expected value of a cycle or a chain, and then the matching algorithm can be used to, for example, find a combination of disjoint cycles and chains that maximizes expected value. One can also combine weights and success probabilities in other ways. Furthermore, as one skilled in the art of optimization can appreciate, the matching algorithm can be used to generate various forms of contingency plans (contingency plans are also referred to as online control policies in optimization literature) that say what cycles and chains should be executed as a function of execution failures and successes in earlier parts of the plan. Furthermore, the contingency plan can include both trade execution actions as well as testing actions (testing additional edges or testing already-tested edges further). In this way, the selected trades and tests that are executed might depend on success and failure of other trades that were planned to be executed earlier as well as success and failure of earlier tests.

Some embodiments provide in an organ exchange that at a fixed duration of time (e.g., once a week) a computer program or the like is run which analyzes available data concerning each donor and potential recipient, confirms or rules out matches, until an exchange plan is generated that includes a set of non-overlapping cycles and chains so as to maximize the sum of the weights of the matched edges.

Embodiments provide that in constructing an exchange plan, multiple testing is performed and the sequence of that testing and the type of testing is variable and does not impact on the embodiments herein. In one non-limiting example in an organ exchange, there are multiple blood tests that might be performed to determine successful edges in an exchange plan. Those multiple tests could be performed on all the proposed edges or merely a few selected edges.

Moreover, embodiments provide that not all edges must be tested. Those skilled in the art will appreciate the different approaches to testing and this disclosure is intended to include all such approaches. Embodiments provide that if one test of an edge fails, no further testing is necessary and that edge is considered failed or bad. Embodiments provide that testing edges and constructing future exchange plans with good edges receiving preference may be continuously accomplished until the exchange plan results in the most number of matches and thus organ, partial organ, or item donations being accomplished within the given pool.

Some embodiments provide for the use of an optimizing algorithm which may generate a plan for testing edges. The plan may include testing one or more edges to determine whether those edges should be tested further, and what other edges should be tested or tested further. This might be accomplished based upon the stored testing data, the created exchange plan, or both. Embodiments provide that the optimization algorithm may use as input the data about successful prior edge tests.

Embodiments provide that a testing plan can be created one step at a time or it can be a multi-step contingency plan. Embodiments provide that a contingency plan may specify in advance which edge tests are to be performed as a function of results from earlier edge tests. Other embodiments provide that the created matching plan may be a contingency plan. Embodiments also provide that a contingency plan may be a joint plan for both trading and testing, i.e. a joint contingency exchange and testing plan. In other words, the trades and tests executed next in the plan may depend on the success or failure of the tests and trades that have occurred in the plan so far. Embodiments provide that this contingency plan might be constructed fully up front or planning might be interleaved with the execution of an exchange plan.

Figure 2:
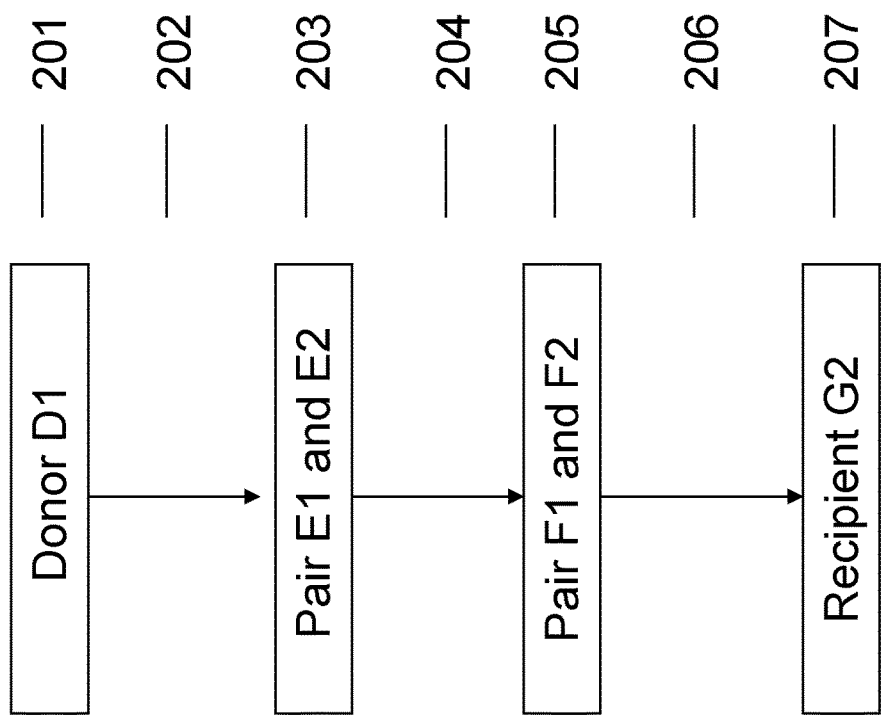
FIG. 2 describes an example barter chain in some embodiments.

Turning now to FIG. 2, a non-limiting example of a barter chain as applied to an organ exchange is described. The chain begins with an altruistic Donor D1 at 201. The unmatched but willing pairs are E (containing donor E1 and patient E2) at 203 and F (containing donor F1 and patient F2) at 205. At the end of the barter chain is vertex G (containing donor G1 and patient G2). G1 is a willing donor but there is no immediate use for that donor in the current pool. Embodiments include using that donor as a bridge donor to start a future chain. Embodiments also include donor G1 donating to a deceased-donor waiting list. There is a match between altruistic Donor D1 and patient E2. Thus, there is an edge at 202 which indicates a planned donation from D1 to E2 which is included in the example exchange plan. Likewise there is match between E1 and F2 and an edge at 204. There is also a match between F1 and G2 resulting in an edge at 206 whereby G2 will receive the donation from F1. Since G2 has no corresponding partner willing to donate in return for G2 receiving what she needs, the chain ends with G2 receiving her donation at 207. Hence, the altruistic Donor D1 begins the chain that leads to G2 receiving her needed organ, partial organ, or item.

Returning to 206 above, suppose that during edge testing the edge F1-G2, first thought compatible by earlier testing, i.e., blood type testing, now tests as incompatible. Embodiments provide that edge 206 (representing the pairing of F1 and G2) is now failed or have become a bad edge. Thus, the entire planned chain from D1 to G2 might be considered failed. Alternatively, the chain up to but not including the edge (206) that caused the failure might still be executed. Embodiments provide that the chain might only be executed at edge 202. Still other embodiments, in other non-limiting examples, provide that any length of a barter chain might be executed but still exclude the failed edge. Embodiments also include re-routing the chain to continue in some other way in light of the failed edge; this re-routing can start from any point in the chain that precedes the failed edge.

Now, returning to FIG. 2, embodiments provide that the remaining edges 202 and 204 are still good. These edges are placed back into the pool of edges. The tested good edges are assigned priorities so that in future construction of exchange plans, the good edges 202 and 204 are preferred over untested edges.

Figure 3:
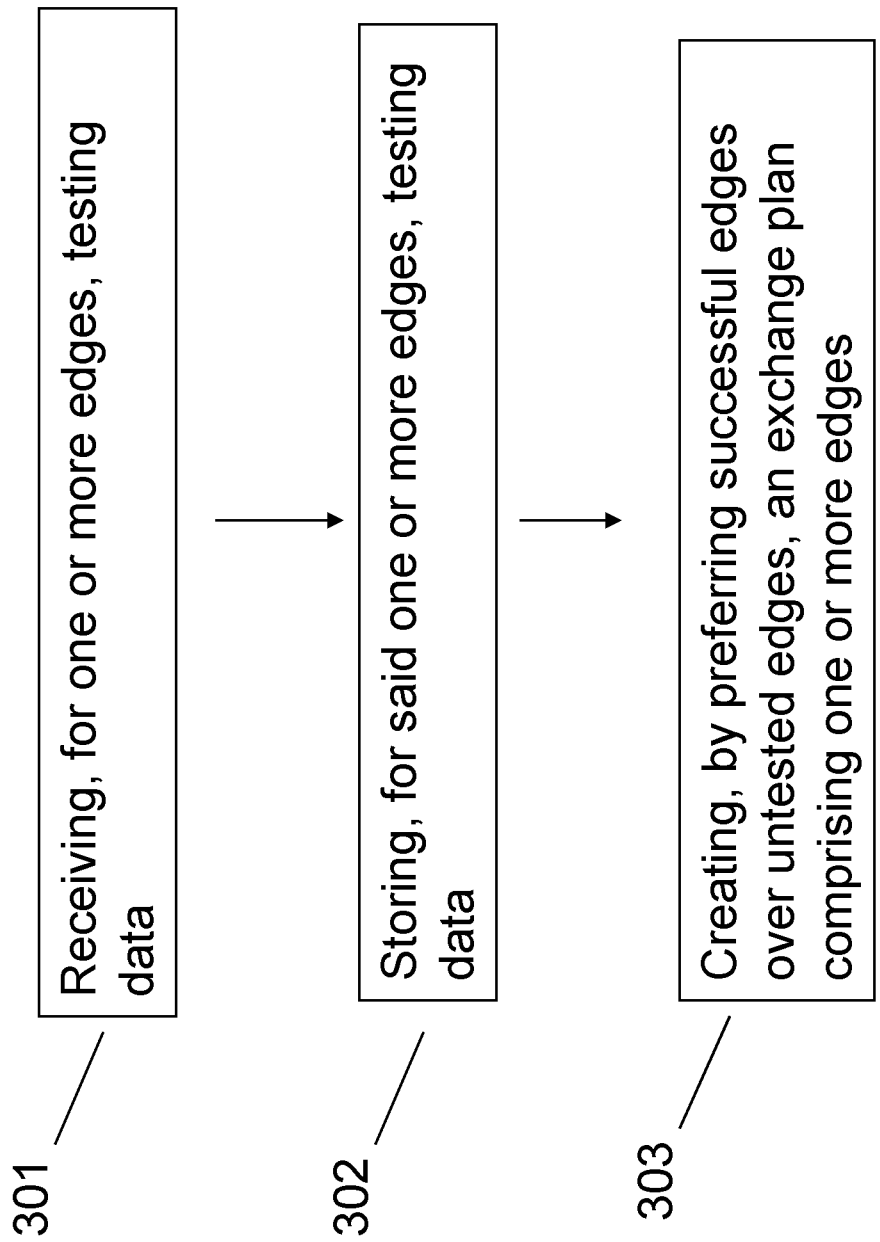
FIG. 3 illustrates an example method of edge tests in barter exchanges.

Now turning to FIG. 3, a non-limiting example embodiment is described. At 301, for one or more edges, testing data, e.g., blood type, tissue type, health, etc. is received. At 302, the data for the one or more edges is stored. At 303, an exchange plan is created by preferring successful edges over untested edges. The exchange plan may comprise successful edges and other types of edges, including untested edges (and potentially even tested and failed edges, although that would not be typical). As discussed above, embodiments provide that in constructing future exchange plans, the successful edges are preferred for inclusion in future exchange plans over untested edges and tested but failed edges.

Figure 4:
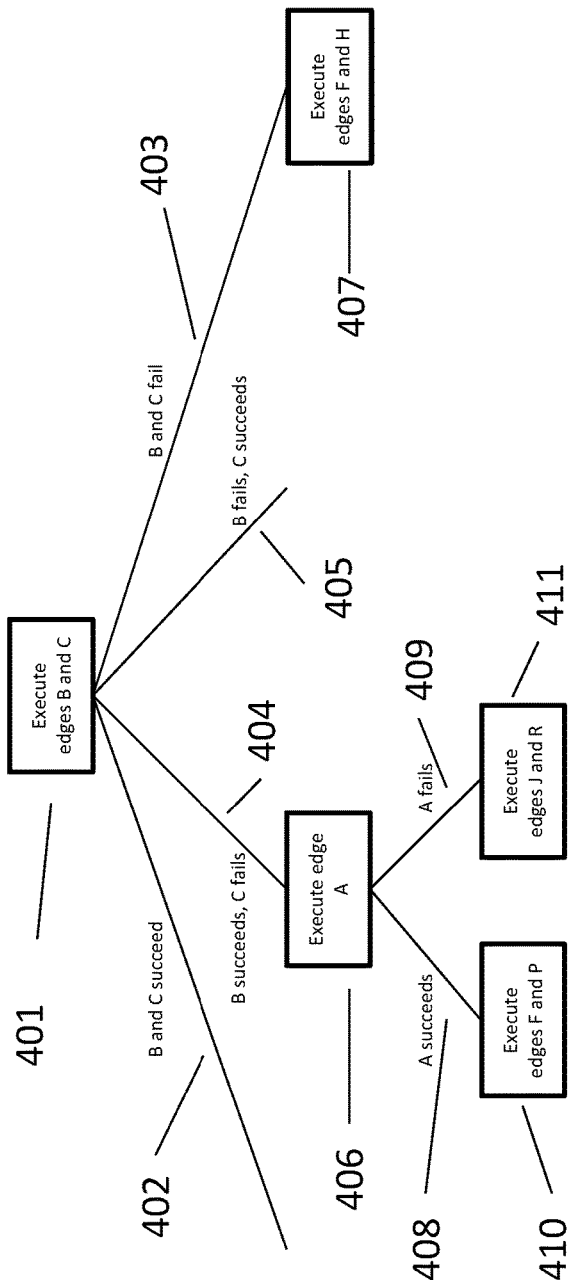
FIG. 4 illustrates an example contingency plan for matching (i.e. trading).
Figure 5:
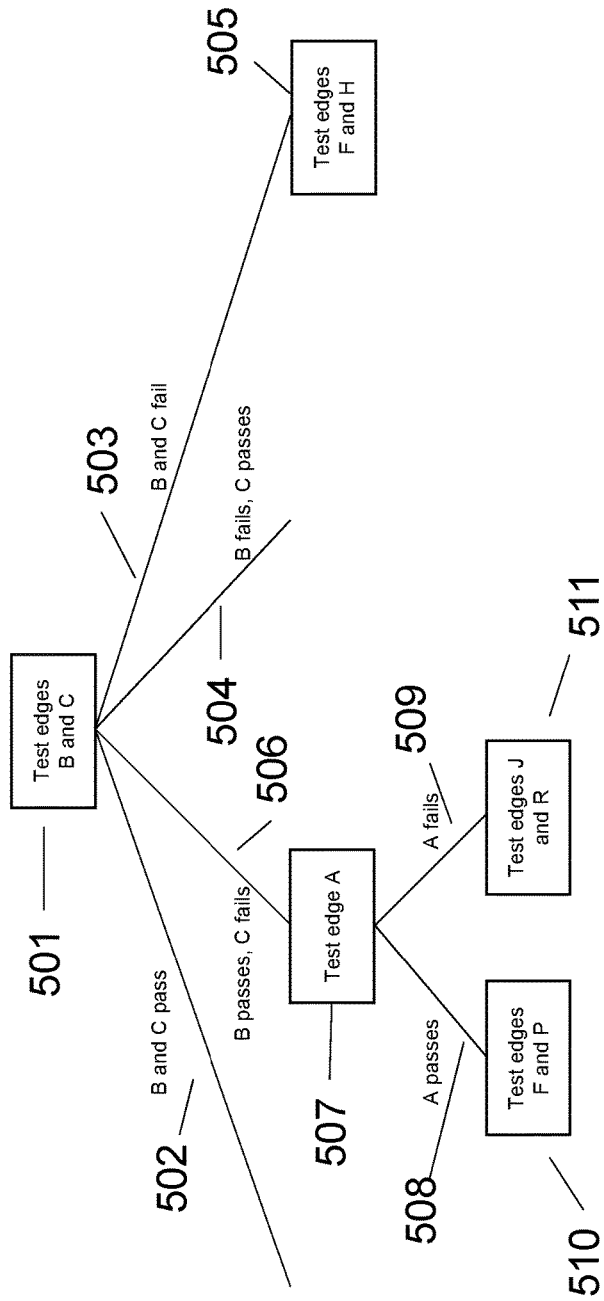
FIG. 5 illustrates a contingency plan for testing.
Figure 6:
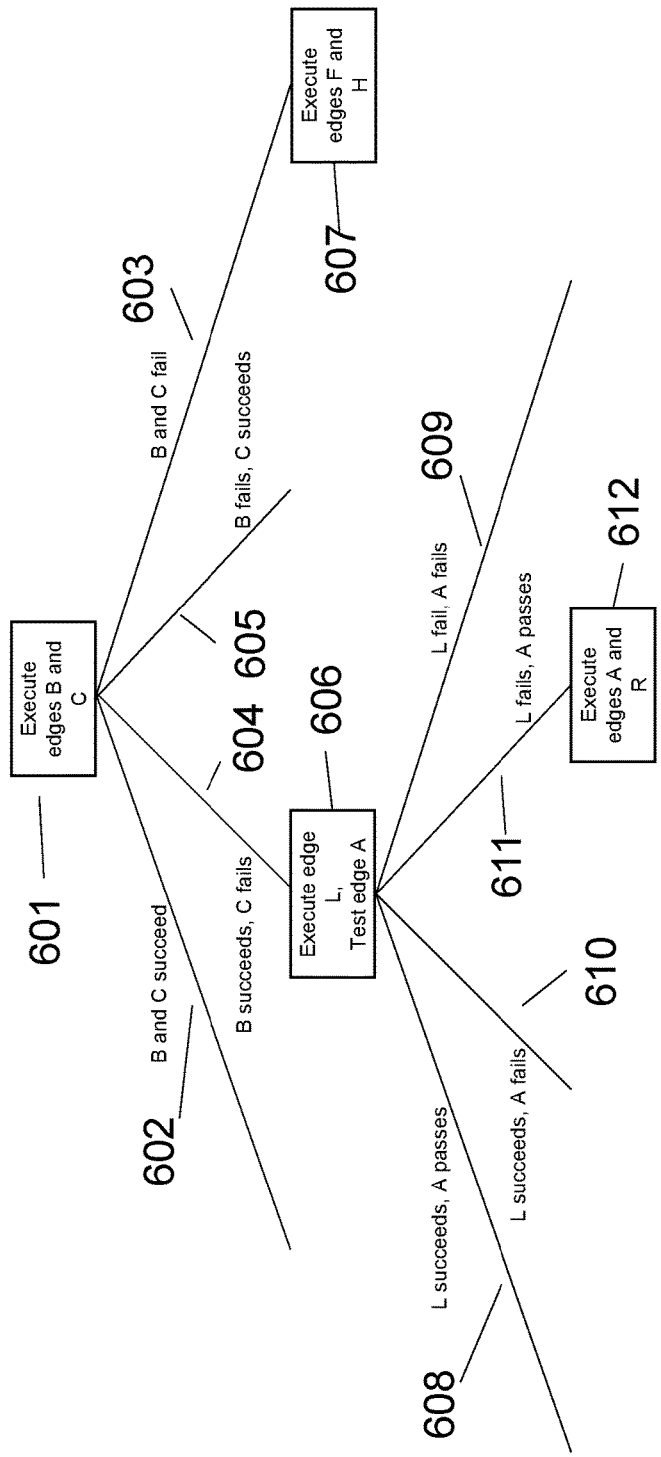
FIG. 6 illustrates a joint contingency plan for matching (i.e. trading) and testing.

Next, the specification turns to example embodiments in FIG. 4-6 of contingency planning. The rectangular nodes are decisions. The connecting lines represent outcomes of those decisions. The plan moves from the top to the bottom down the lines.

Now turning to FIG. 4, an example embodiment of a contingency plan for matching (i.e. trading) is shown. At 401, the plan executes edges B and C. At 402, edge B and C are successful. At 403, edge B and C fail, thus at 407, the plan executes edges F and G. At 404, edge B succeeds and edge C fails, thus at 406, edge A is executed. At 408, edge A succeeds, thus at 410, edges F and P are executed. At 409, edge A fails, thus at 411, edges J and R are executed.

Now turning to FIG. 5, an example embodiment of a contingency plan for testing is shown. At 501, edges B and C are tested. At 502, edges B and C pass the test. At 503, both edges B and C fail the test. Thus at 505, edges F and H are tested. At 504, edge B fails and edge C passes. At 506, edge B passes the test but edge C fails the test. Thus, at 507 edge A is tested. At 508, edge A passes the test. Thus at 510, edges F and P are tested. However, at 509 if edge A fails the test, the contingency plan then calls for testing edges J and R at 511.

Now turning to FIG. 6, an example embodiment of a joint contingency plan for matching (i.e. trading) and testing is shown. At 601, edges B and C are executed. At 602, edges B and C succeed. However, at 603, edges B and C fail, thus the plan calls for executing edges F and H at 607. At 604, edge B succeeds but edge C fails, thus at 606, the plan calls for executing edge L and testing edge A. At 605, edge B fails and edge C succeeds. At 608, edge L succeeds and edge A passes. At 609, edge L fails and edge A fails. At 610, edge L succeeds and edge A fails. At 611, edge L fails and edge A passes. Thus, the plan calls for executing edge A and R at 612.

Embodiments provide that the results of testing and execution discussed in FIG. 4-7, need not be thought of as strictly pass or fail or succeed or fail. The results might also be various degrees of passing and success. The contingencies in the contingency plans might be based upon those various degrees. Additionally, when discussing whether an edge or exchange would likely succeed or likely fail, this may not be an absolute. For example, an edge that is identified as likely to succeed may not only be an edge that has an over 50% chance of success. Rather, an edge that is likely to succeed may include an edge that has more chance of succeeding than another edge. For example, if one edge has a chance of success of 5% and another has a chance of success of 1%, the edge having the chance of success of 5% may be considered likely to succeed as compared to the 1% edge. Thus, the likeliness of success of an edge may be attributed to the chance of success as compared to other edges that could be used in the place of that edge. In other words, if three exchanges could be used for an edge between two nodes, the chosen edge may be the edge that is likely to succeed as compared to the other edges.

It will be appreciated by those skilled in the art that within a particular exchange plan, there can be multiple cycles, chains, and combinations all working in parallel or concurrently. This disclosure contemplates all such combinations and embodiments within this disclosure may be accomplished using any of these combinations or at least one cycle or at least one chain.

In this way, at least one embodiment provides systems and methods for collecting, processing, storing, and providing all the information so that the necessary and optimum trades can be accomplished among and between the vertices.

Embodiments provide an interior of such a chain is like that of a cycle with each participant in the interior of the chain giving some item(s) and receiving some item(s). Embodiments described that each leg of the chain can involve more than one item. A chain can end in various ways. It will be appreciated that these example chain endings are not meant to be exhaustive and anybody skilled in the relevant art will understand the myriad of endings available for a chain, which are contemplated by the instant disclosure.

In one non-limiting example, an embodiment provides for a chain ending when some participant receives an item without any expectation that participant gives an item. Other embodiments allow the chain to end when the last participant donates his/her item to charity. Still other embodiments provide that the last participant in the chain becomes a "stand-in" altruist to trigger a new chain with at least one item from among the item(s) that he/she would have been willing to give out in trade for the item(s) that he/she received. Other embodiments end the chain with the sale of the item(s) that the last participant in the chain was willing to trade in consideration for the item he received and/or some of the items he received. Other embodiment provide for continuous or new chain formation such that there is not a strict ending to a given chain so much as components or legs thereof have been accomplished.

Embodiments provide barter legs that may be accomplished contemporaneously, concurrently, or in any other desirable order and there are no constraints on the sequence or number of barter trades contemplated herein. In one non-limiting example returning to FIG. 2, leg 204 could be accomplished before leg 202. Alternatively, leg 206 and leg 202 could be accomplished simultaneously. Embodiments do not limit the sequencing or number of such legs in an exchange plan.

Some example embodiments, without limitation, may be applied to transplantation, such as liver lobes, multiple different organs, bone marrow, or any other body parts. Embodiments are not limited to organ exchanges, but are also applicable to used and new goods, services, time allocations, and so on. All such applications are contemplated within this disclosure. It will be appreciated by those who are skilled in the relevant art that embodiments may be practiced using any useful tests and this disclosure contemplates using any such tests.

Further non-limiting example embodiments describe exchange plans applied to intangible rights such as time shares or patent licensing. Still other embodiments involve barter of service for services or services for goods or donation of services. The items being traded can be anything. The combination and types of items are unlimited.

As a non-limiting example, an embodiment may receive (for example, via transmission over a network connection, such as the Internet or a WAN/telecommunications network, to an appropriate interface of an electronic device) information from and about exchange plan participants. The information may comprise personally identifiable information needed to identify and track medical patients, such as name, social security number, date of birth, geographic location, etc. It may comprise information about health condition, blood type, tissue, and whether a match has been identified, and the identification of such match, etc.

An embodiment may store the information thus received, for example in a tangible memory device to build up one more repositories of information used in connection with the barter chain functionality described herein. An embodiment may also collect such information, for example via providing a downloadable application to a device. The downloadable application may include one or more templates for organizing and facilitating collection of the information that, once entered into the downloadable application (downloaded onto a participant's device, such as a mobile phone or computing device) allows an embodiment to either receive or actively collect the item information. A similar mechanism may be provided for other information, such as participant personal information, for example.

An embodiment may process the information, for example providing categorizing functions that organize the received information. For example, the received information may be linked or otherwise associated to one or more other donors or potential recipients as required and also analyzed for suitability with respect to one or more existing or future exchange plans. Accordingly, and embodiment may receive item information and store it, before or after processing it.

An embodiment may facilitate an exchange plan formation, progression or completion by automatically suggesting potential edges (matching donor-potential recipient pairs). The suggested item or items may include either items from a stored repository of donated organs, partial organs, or items from a stored repository of donated items. An embodiment may facilitate the exchange plan formation, progression or completion by actively transmitting information to one or more participants or potential participants, for example via transmission of the suggestion to a participant's device (such as a mobile phone or computing device) via a suitable network connection. Alternatively, an embodiment may provide such suggestions, including suggested matches of particular organs, partial organs, or items, or goods, cycles or chains.

An embodiment may facilitate participant involvement by soliciting for needed organs, partial organs, or items or participants, either as barter items or as donated items and like participants, to one or more users of the system. An embodiment may achieve such solicitation by mechanisms commensurate with those described above for receiving, storing and processing information and facilitating barter chains. Accordingly, and embodiment may analyze one or more barter chains or cycles, one or more participants' information, one or more repositories of items, or a suitable combination thereof, in order to actively solicit participant involvement.

As will be appreciated by one skilled in the art, various aspects may be embodied as an apparatus, system, method or program product. Accordingly, aspects may take the form of an entirely hardware embodiment or an embodiment including software that may all generally be referred to herein as a "circuit," "module" or "system." Furthermore, aspects may take the form of a program product embodied in one or more device readable medium(s) having device readable program code embodied therewith.

Any combination of one or more non-signal device readable medium(s) may be utilized. The non-signal medium may be a storage medium, such as a memory included in or associated with video data processing device.

Program code embodied on a non-signal storage medium may be transmitted using any appropriate medium, including but not limited to wireless, wireline, optical fiber cable, RF, et cetera, or any suitable combination of the foregoing. Program code for carrying out operations may be written in any combination of one or more programming languages. The program code may execute entirely on a single device, partly on a single device, as a stand-alone software package, or partly on single device and partly on another device. In some cases, the devices may be connected through any type of connection, either a physical (wired connection, such as over a USB connection) or via a network, including a local area network (LAN) or a wide area network (WAN), or the connection may be made through other devices (for example, through the Internet using an Internet Service Provider).

Embodiments are described with reference to figures of methods, devices, and program products. It will be understood that portions of the figures can be implemented by program instructions. These program instructions may be provided to processor(s) of a programmable data processing device to produce a machine, such that the instructions, which execute via the processor(s) of the programmable data processing device create a means for implementing the functions/acts specified.

The program instructions may also be stored in a device readable storage medium that can direct a programmable data processing device to function in a particular manner, such that the instructions stored in the storage medium produce an article of manufacture including instructions which implement the function/act specified. The program instructions may also be loaded onto a programmable data processing device to cause a series of operational steps to be performed on the programmable device to produce a process such that the instructions which execute on the programmable device provide processes for implementing the functions/acts specified.

Figure 7:
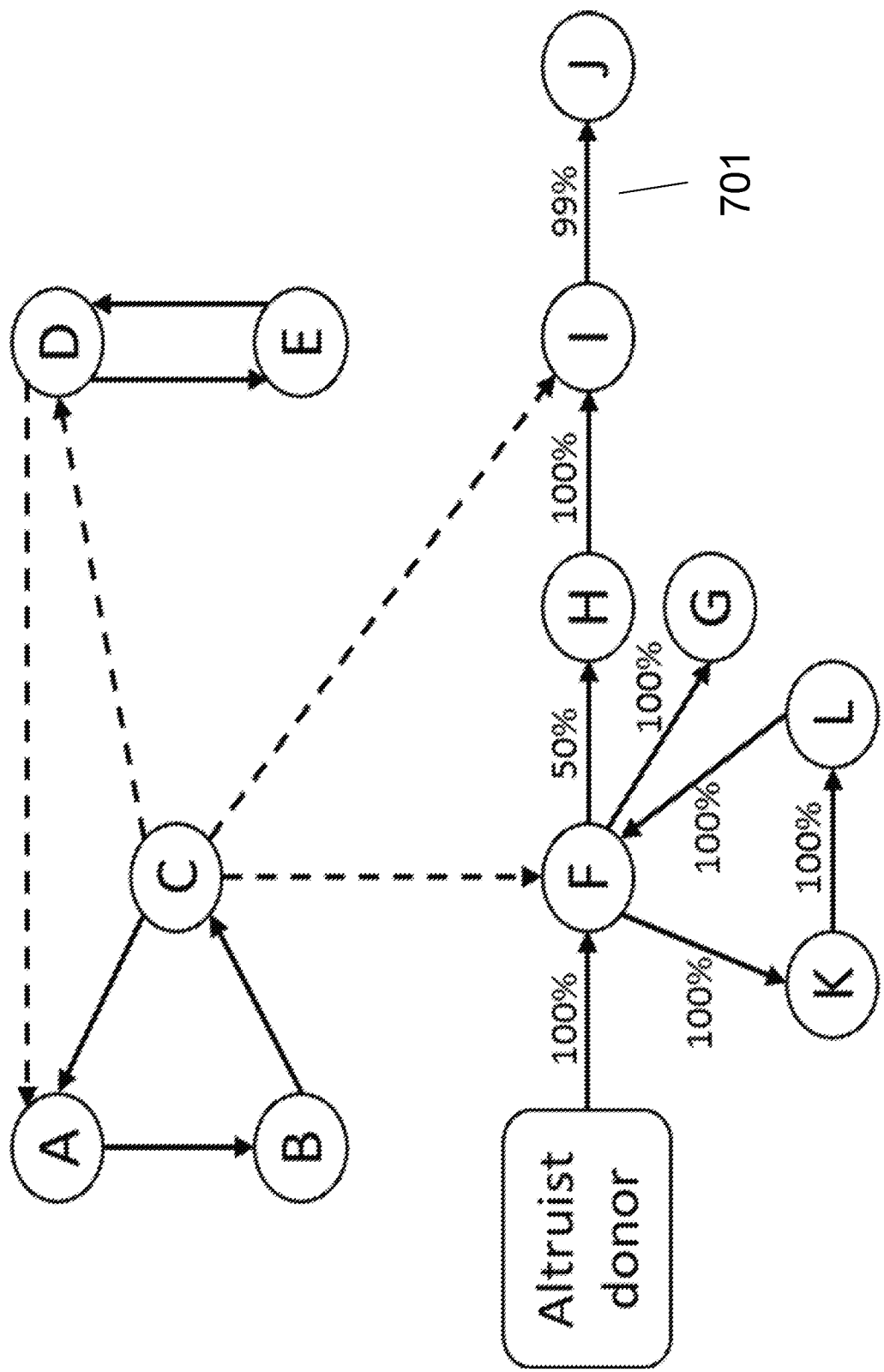
FIG. 7 illustrates an example input graph.

Referring now to FIG. 7, an example input graph is illustrated that illustrates an example barter chain exchange plan. The edges 701 represent compatibility. In FIG. 7, for simplicity, the weights of the edges are not shown, and the percentages on edges 701 are the success probabilities. This figure will be used in the following example.

Expected Values of Cycles and Chains

In this example, there are three cycles that can be used for exchanging. One cycle is A→B→C→A, another is D→E→D, and the third is F→K→L→F. Clearly, it is best to include the first two of these cycles in the exchange plan—regardless of the weights and success probabilities of the edges in those cycles—because the vertices in those cycles cannot participate in any other way of exchanging. The dashed edges in the figure show compatibilities that cannot be used for exchanging because they cannot be part of a cycle or a chain that emanates from an altruist.

There is one altruist in this example that can trigger alternative chains:

Altruist→F
Altruist→F→G
Altruist→F→H
Altruist→F→H→I
Altruist→F→H→I→J

The expected value of a cycle=(product of success probabilities of edges in the cycle)*(sum of edge weights in the cycle). This is assuming the cycle fails if even one edge in it fails.

The expected value of a chain=sum over possible successful execution lengths of the chain of (product of success probabilities up to that execution length)*(edge weights at that length). This assumes that a head of a chain can execute up to, but not including, the failed edge. For example, in the figure, the expected value of a chain Altruist→F→H→I→J (assuming all edge weight are 1 for simplicity) is

100%*1+
100%*50%*1+
100%*50%*100%*1+
100%*50%*100%*99%*1
=1+0.5+0.5+0.495=2.495

Generating an Exchange Plan

So, given that one cannot use vertex F both in a chain and the cycle F→K→L→F, it is best not to include a chain in the exchange plan but to include cycle F→K→L→F because its expected value is 3 (assuming, for simplicity, that all three edges have weight 1), and 3>2.495.

One can generate as the exchange plan the highest-expected-value combination of disjoint cycles and chains, that is combination of cycles and chain that do not share vertices. This can be done, for example, with the following algorithm.

Pseudocode for finding an exchange plan that is the highest-expected-value combination of disjoint cycles and chains:

1. Generate all cycles in the input graph (no longer than a cycle-length cap if such a cap is desired). This can be done using depth-first-search in the input graph.
2. Generate a binary variable for each such cycle.
3. Generate all chains (no longer than a chain-length cap if such a cap is desired). This can be done using depth-first-search in the input graph.
4. Generate a binary variable for each such chain.
5. For all pairs of structures (cycles and chains), if the two structures in the pair share a vertex, then include a constraint that states that no more than one of the respective two binary variables can take on value 1. Value 1 represents that structure being included in the exchange plan, and value 0 represents that structure not being included in the exchange plan.
6. Set the objective of the problem to be maximizing expected value. In other words, if we denote the binary variables by $x_i$ and the expected values of the respective structures (as defined above) by $v_i$, the mathematical objective is max $\Sigma_i v_i * x_i$
7. Run an Integer Program Solver, Such as the IBM® ILOG CPLEX Optimization Studio or Gurobi Optimizer or a Custom Solver, to Solve this Model.

For the example input graph in FIG. 7, this pseudocode would return as the exchange plan the three different cycles A→B→C→A, D→E→D, and F→K→L→F.

Incorporate New Testing Results

One can incorporate new testing results, for example, by updating the edge probabilities and then rerunning the pseudocode above. For example, if we test the 50% edge F→H, and the test comes back estimating that the success probability is 99%, then it is better to include the chain Altruist→F→H→I→J in the exchange plan than the cycle F→K→L→F. This is because the expected value of the chain would be 100%*1+
100%*99%*1+
100%*99%*100%*1+
100%*99%*100%*99%*1
=1+0.99+0.99+0.9801=3.9601 a number which is greater than the expected value 3 available from the cycle.

Generating Contingency Plans

One way to generate contingency plans (contingent plans) in this setting is to see what would be the best solution if some edge, or combination of edges, in the exchange plan failed. To accomplish this, one can remove those edges from the input graph and rerun the pseudocode above. For example, if edge F→H failed (despite having success probability 99%) the best (and only) contingency would be to extend the chain Altruist→F to be Altruist→F→G.

Determining which Edge, or Combination of Edges to Test

One can also use this to determine which edge, or combination of edges, to test (and in which order, and where a predetermined number of edges can potentially be tested in parallel). There are many ways to do this.

In one non-limiting example, one can see which edge would be most worth testing as follows.

For each edge:

For each possible scenario (i.e., success probability) that might be the result of the test on that edge (these values can be discretized to keep the complexity low):

Run the pseudocode above to determine the exchange plan and its value in that scenario.

Sum up those values, weighing them by the probability of how likely each of the scenarios is.

Choose the edge to test that gives the highest sum.

This can be extended to selecting a testing plan that can involve testing multiple edges in parallel and sequentially. We just generalize the notion of scenario to not only include the possible results of one edge test but combinations of edge tests, where in the testing policy the sequentially later tests to conduct can depend on the outcomes of the tests conducted so far. Finally, choose the testing plan that gives the highest sum.

Referring now to FIG. 8, an example device that may be used in implementing one or more embodiments includes a computing device in the form of a computer 810. Components of computer 810 may include, but are not limited to, a processing unit 820, a system memory 830, and a system bus 822 that couples various system components including the system memory 830 to the processing unit 820. Computer 810 may include or have access to a variety of computer readable media. The system memory 830 may include computer readable storage media, for example in the form of volatile and/or nonvolatile memory such as read only memory (ROM) and/or random access memory (RAM). By way of example, and not limitation, system memory 830 may also include an operating system, application programs, other program modules, and program data.

A user can interface (for example, enter commands and information) into the computer 810 through input devices 840. A monitor or other type of device can also be connected to the system bus 822 via an interface, such as an output interface 850. In addition to a monitor, computers may also include other peripheral output devices. The computer 810 may operate in a networked or distributed environment using logical connections to one or more other remote device(s) 870 such as other computers. The logical connections may include network interface(s) 860 to a network, such as a local area network (LAN), a wide area network (WAN), and/or a global computer network, but may also include other networks/buses.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. An exchange plan system for testing exchanges from a pool of nodes and generating, from the pool, an organ exchange plan, comprising:
    a processor;
    a memory in communication with the processor; and
    a computer readable program executable by the processor and configured to:
    access, using the processor of the exchange plan system, from the memory, a pool of potential nodes representing organs to be exchanged within an organ exchange program, wherein each of the potential nodes represents one of: a pair comprising both at least one organ to be given and at least one organ to be received in an exchange and an organ to be given or received in an exchange;
    test, using the processor of the exchange plan system, one or more edges between at least a subset of the pool of potential nodes, wherein the testing comprises determining a compatibility between nodes connected by each of the one or more edges, wherein an edge represents an exchange between two of the potential nodes;
    store, within the memory of the exchange plan system, test data corresponding to the tests with a corresponding edge, wherein the storing comprises identifying each edge as one of: a failed edge, a successful edge, and an untested edge, wherein a successful edge represents a tested edge indicating an exchange along that edge has a higher percentage chance of success as compared with at least one other edge, wherein a successful edge represents an exchange between nodes connected by the successful edge having test data indicating at least a partial match between an organ to be given and an organ to be received, wherein the storing comprises assigning a dynamic priority to a successful edge indicating a priority of the successful edge over an untested edge and a failed edge; and
    create, using the processor of the exchange plan system, as an output of an optimization, a final exchange plan, wherein the final exchange plan identifies a plurality of transplants of organs represented by the nodes and corresponding to an entity presenting a corresponding organ within the final exchange plan, the final exchange plan comprising at least one of a chain and a cycle identified by running the optimization, wherein the final exchange plan has an input comprising at least one successful edge retrieved from the memory and selected based upon the dynamic priority assigned to the at least one successful edge; and
    the running the optimization comprises creating a plurality of exchange plans from at least chains and cycles from the nodes and identifying a resulting value for each of the plurality of exchange plans, and maximizing, by evaluating an objective function using the processor of the exchange plan system, a resulting value for the final exchange plan via identifying a combination of at least chains and cycles from the plurality of exchange plans having a highest resulting value, wherein the resulting value is based upon (i) success probabilities of edges within the chains and cycles and (ii) edge weights in the chains and cycles, wherein the running the optimization comprises incorporating new test results by updating the dynamic priority of an edge and rerunning the optimization.

2. The system of claim 1, wherein the test data indicating at least a partial match are based at least in part on at least one set of data selected from the group consisting of: blood crossmatching, tissue crossmatching, health status of donor, health status of recipient, donor availability, recipient availability, donor eligibility, and recipient eligibility.

3. The system of claim 1, wherein the optimization finds at least one set of non-overlapping chains comprising edges.

4. The system of claim 1, wherein the optimization comprises assigning a priority to the one or more successful edges.

5. The system of claim 1, wherein the optimization comprises assigning a weight to each of the one or more successful edges.

6. The system of claim 1, wherein the optimization comprises assigning a probability of success to each of the one or more successful edges.

7. The system of claim 1, wherein the optimization comprises assigning a weight and probability of success to each of the one or more successful edges.

8. The system of claim 1, further comprising the step of analyzing, wherein analyzing comprises determining which one or more edges should be tested or tested further, based on the stored testing data, or the stored testing data and the created exchange plan.

9. The system of claim 1, further comprising constructing a contingency plan of which edges to test or test further based on the stored testing data, or the stored testing data and the created exchange plan.

10. The system of claim 1, wherein the exchange plan is a contingency plan.

11. The system of claim 1, wherein the exchange plan is a joint contingency exchange and testing plan.

12. The system of claim 1, further comprising obtaining at least one element selected from the group consisting of one or more untested edges between nodes and one or more failed edges between nodes, wherein the one or more failed edges represent a tested edge indicating an exchange along that edge has a lower percentage chance of success as compared with at least one other edge.

13. A program product of an exchange plan system for testing exchanges from a pool of nodes and generating, from the pool, an organ exchange plan, comprising:
    a non-transitory computer readable storage medium having computer readable program code embodied therewith, the computer readable program code configured to operate the exchange plan system to perform acts comprising:

accessing, using a processor of the exchange plan system and from a memory of the exchange plan system, a pool of potential nodes representing organs to be exchanged within an organ exchange program, wherein each of the potential nodes represents one of: a pair comprising both at least one organ to be given and at least one organ to be received in an exchange and an organ to be given or received in an exchange;

testing, using the processor of the exchange plan system, one or more edges between at least a subset of the pool of potential nodes, wherein the testing comprises determining a compatibility between nodes connected by each of the one or more edges, wherein an edge represents an exchange between two of the potential nodes;

storing, within the memory of the exchange plan system, test data corresponding to the tests with a corresponding edge, wherein the storing comprises identifying each edge as one of: a failed edge, a successful edge, and an untested edge, wherein a successful edge represents an exchange between two of the potential nodes, wherein the one or represents a tested edge indicating an exchange along that edge has a higher percentage chance of success as compared with at least one other edge, wherein a successful edge represents an exchange between nodes connected by the successful edge having test data indicating at least a partial match between an organ to be given and an organ to be received, wherein the storing comprises assigning a dynamic priority to a successful edge indicating a priority of the successful edge over an untested edge and a failed edge; and creating, using the processor of the exchange plan system, as an output of an optimization, a final exchange plan, wherein the final exchange plan identifies a plurality of transplants of organs represented by the nodes and corresponding to an entity presenting a corresponding organ within the final exchange plan, the final exchange plan comprising at least one of a chain and a cycle identified by running the optimization, wherein the final exchange plan has an input comprising at least one successful edge retrieved from the memory and selected based upon the dynamic priority assigned to the at least one successful edge; and the running the optimization comprises creating a plurality of exchange plans from at least chains and cycles from the nodes and identifying a resulting value for each of the plurality of exchange plans, and maximizing, by evaluating an objective function using the processor of the exchange plan system, a resulting value for the final exchange plan via identifying a combination of at least chains and cycles from the plurality of exchange plans having a highest resulting value, wherein the resulting value is based upon (i) success probabilities of edges within the chains and cycles and (ii) edge weights in the chains and cycles, wherein the running the optimization comprises incorporating new test results by updating the dynamic priority of an edge and rerunning the optimization.

14. The program product of claim 13, wherein the test data indicating at least a partial match are based at least in part on at least one set of data selected from the group consisting of: blood crossmatching, tissue crossmatching, health status of donor, health status of recipient, donor availability, recipient availability, donor eligibility, and recipient eligibility.

15. The program product of claim 13, wherein the optimization finds at least one set of non-overlapping chains comprising edges.

16. The program product of claim 13, wherein the optimization comprises assigning a priority to each of the one or more successful edges.

17. The program product of claim 13, wherein the optimization comprises assigning a weight to each of the one or more successful edges.

18. The program product of claim 13, wherein the optimization comprises assigning a weight and probability of success to each of the one or more successful edges.

19. The program product of claim 13, further comprising the step of analyzing, wherein analyzing comprises determining which one or more edges should be tested or tested further, based on the stored testing data, or the stored testing data and the created exchange plan.

20. The program product of claim 13, further comprising the step of analyzing, wherein analyzing comprises constructing a contingency plan of which edges to test or test further based on the stored testing data, or the stored testing data and the created exchange plan.

21. The program product of claim 13, further comprising obtaining at least one element selected from the group consisting of one or more untested edges between nodes and one or more failed edges between nodes, wherein the one or more failed edges represent a tested edge indicating an exchange along that edge has a lower percentage chance of success as compared with at least one other edge.

22. A method for testing exchanges from a pool of nodes and generating, from the pool, an organ exchange plan using an exchange plan system, comprising:

accessing, using a processor of the exchange plan system, from a memory of the exchange plan system, a pool of potential nodes representing organs to be exchanged within an organ exchange program, wherein each of the potential nodes represents one of: a pair comprising both at least one organ to be given and at least one organ to be received in an exchange and an organ to be given or received in an exchange;

testing, using the processor of the exchange plan system, one or more edges between at least a subset of the pool of potential nodes, wherein the testing comprises determining a compatibility between nodes connected by each of the one or more edges, wherein an edge represents an exchange between two of the potential nodes;

storing, within the memory of the exchange plan system, test data corresponding to the tests with a corresponding edge, wherein the storing comprises identifying each edge as one of: a failed edge, a successful edge, and an untested edge, wherein a successful edge wherein the one or more successful edges represents a tested edge indicating an exchange along that edge has a higher percentage chance of success as compared with at least one other edge, wherein a successful edge represents an exchange between nodes connected by the successful edge having test data indicating at least a partial match between an organ to be given and an organ to be received, wherein the storing comprises assigning a dynamic priority to a successful edge indicating a priority of the successful edge over an untested edge and a failed edge; and creating, using the processor of the exchange plan system, as an output of an optimization, a final exchange plan, wherein the final exchange plan identifies a plurality of transplants of organs represented by the nodes and corresponding to an entity presenting a corresponding organ within the final exchange plan, the final exchange plan comprising at least one of a chain and a cycle identified by running the optimization, wherein the final exchange plan has an input comprising at least one successful edge retrieved from the memory and selected based upon the dynamic priority assigned to the at least one successful edge; and the running the optimization comprises creating a plurality of exchange plans from at least chains and cycles from the nodes and identifying a resulting value for each of the plurality of exchange plans, and maximizing, by evaluating an objective function using the processor of the exchange plan system, a resulting value for the final exchange plan via identifying a combination of at least chains and cycles from the plurality of exchange plans having a highest resulting value, wherein the resulting value is based upon (i) success probabilities of edges within the chains and cycles and (ii) edge weights in the chains and cycles, wherein the running the optimization comprises incorporating new test results by updating the dynamic priority of an edge and rerunning the optimization.

23. The method of claim 22, further comprising obtaining at least one element selected from the group consisting of one or more untested edges between nodes and one or more failed edges between nodes, wherein the one or more failed edges represent a tested edge indicating an exchange along that edge has a lower percentage chance of success as compared with at least one other edge.

\* \* \* \* \*